United States Patent
Hwang et al.

(10) Patent No.: US 9,097,970 B2
(45) Date of Patent: Aug. 4, 2015

(54) PHOTOREFRACTIVE COMPOSITE, SPATIAL LIGHT MODULATOR, AND HOLOGRAM DISPLAY DEVICE USING THE SAME

(71) Applicant: Samsung Electronics Co., Ltd., Suwon-Si, Gyeonggi-Do (KR)

(72) Inventors: Kyu-young Hwang, Ansan-si (KR); Gae-hwang Lee, Hwaseong-si (KR); Jae-eun Jung, Seoul (KR); Chil-sung Choi, Suwon-si (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 300 days.

(21) Appl. No.: 13/708,121

(22) Filed: Dec. 7, 2012

(65) Prior Publication Data

US 2013/0148181 A1 Jun. 13, 2013

(30) Foreign Application Priority Data

Dec. 8, 2011 (KR) .......... 10-2011-0131115
Dec. 7, 2012 (KR) .......... 10-2012-0142241

(51) Int. Cl.
*G03H 1/02* (2006.01)
*G03F 7/027* (2006.01)
(Continued)

(52) U.S. Cl.
CPC ............... *G03F 7/027* (2013.01); *C07C 13/28* (2013.01); *C07C 15/18* (2013.01); *G02B 5/32* (2013.01);
(Continued)

(58) Field of Classification Search
CPC ......... G03F 7/027; G03F 7/105; G03F 7/001; G03F 7/031; C07C 15/18; C07C 13/28; G03H 1/0476; G03H 1/12; G03H 1/2294; G03H 2260/54; G03H 2225/25; G02B 26/02; G02B 26/06; G02B 5/32; G02B 26/00
See application file for complete search history.

(56) References Cited

U.S. PATENT DOCUMENTS 3,711,180 A * 1/1973 Klinger et al. ............... 359/252
5,361,148 A * 11/1994 Bjorklund et al. ............... 359/4
(Continued)

FOREIGN PATENT DOCUMENTS

JP 2001-066651 A 3/2001
JP 2001-247577 A 9/2001
(Continued)

OTHER PUBLICATIONS

Dash et al. "Polyhedral boron clusters in materials science", New. J. Chem., vol. 35 pp. 1955-1972 (Oct. 2011).*
(Continued)

*Primary Examiner* — Martin Angebranndt
(74) *Attorney, Agent, or Firm* — Harness, Dickey & Pierce, P.L.C.

(57) ABSTRACT

A photorefractive composite, a spatial light modulator and a hologram display device using the same include at least one carborane compound expressed as the following Chemical Formulae 1A through 1C:

Chemical Formula 1A

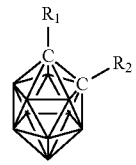

Chemical Formula 1B

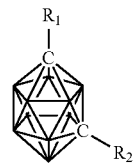

Chemical Formula 1C

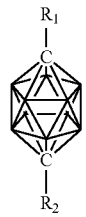

wherein the photorefractive composite exhibits photoconductivity and optical nonlinearity.

29 Claims, 4 Drawing Sheets

(51) Int. Cl.
  *G03F 7/031* (2006.01)
  *C07C 13/28* (2006.01)
  *G02B 26/00* (2006.01)
  *G03H 1/12* (2006.01)
  *G02B 26/02* (2006.01)
  *G02B 26/06* (2006.01)
  *G02B 5/32* (2006.01)
  *G03H 1/04* (2006.01)
  *C07C 15/18* (2006.01)
  *G03F 7/00* (2006.01)
  *G03F 7/105* (2006.01)
  *G03H 1/22* (2006.01)
  *G03H 1/18* (2006.01)
  *G03H 1/26* (2006.01)

(52) U.S. Cl.
  CPC ............... *G02B 26/00* (2013.01); *G02B 26/02* (2013.01); *G02B 26/06* (2013.01); *G03F 7/001* (2013.01); *G03F 7/031* (2013.01); *G03F 7/105* (2013.01); *G03H 1/0476* (2013.01); *G03H 1/12* (2013.01); *G03H 1/2294* (2013.01); *G03H 2001/0264* (2013.01); *G03H 2001/183* (2013.01); *G03H 2001/2655* (2013.01); *G03H 2225/25* (2013.01); *G03H 2260/54* (2013.01)

(56) References Cited

U.S. PATENT DOCUMENTS

| 2004/0200999 | A1  | 10/2004 | Cammack et al. |         |
|---|---|---|---|---|
| 2004/0242841 | A1* | 12/2004 | Cammack et al. | 528/481 |
| 2010/0099789 | A1  | 4/2010  | Gu et al. |         |
| 2012/0319088 | A1* | 12/2012 | Lee et al. | 257/40 |
| 2013/0148180 | A1* | 6/2013  | Hwang et al. | 359/11 |

FOREIGN PATENT DOCUMENTS

| JP | 2005-162709 | A | 6/2005 |
| JP | 2005-166574 | * | 6/2005 |
| WO | 2012/018342 | * | 2/2012 |

OTHER PUBLICATIONS

Songkram et al. "Conformational control of benzyl-o-carboranylbenzene derivatives . . . ", Inorg. Chem., vol. 49 pp. 11174-11183 (Nov. 2010).*

Jiang et al., "Synthesis and structural charachterization of bis and tris(closo-1,2-C2B10H11-1-y1) substituted . . . " Inorg chem., vol. 35 pp. 3056-3058 (1996).*

Jankowiak et al., "Ring-alkyl connecting gropup effectr on mesogenic properties of p-carborane derivatives and their . . . ", Beil. J Org. Chem., vol. 5(83) 10 pages (2009).*

Blanche, P.-A. et al. "Holographic three-dimensional telepresence using large-area photorefractive polymer"; Nature, vol. 468, pp. 80-83; Nov. 4, 2010.

Tay, S. et al. "An updated holographic three-dimensional display"; Nature, vol. 451, pp. 694-698; Feb. 7, 2008.

Office Action for U.S. Appl. No. 13/679,359 dated Nov. 26, 2014.

Christenson et al., "Grating dynamics in a photorefractive polymer with Alq3 eletron traps," Optics Express, 2010, vol. 18, No. 9, pp. 9358-9365, Optical Society of America.

* cited by examiner

PHOTOREFRACTIVE COMPOSITE, SPATIAL LIGHT MODULATOR, AND HOLOGRAM DISPLAY DEVICE USING THE SAME

CROSS-REFERENCE TO RELATED APPLICATIONS

This application claims the benefit of priority under 35 U.S.C. §119(e) to Korean Patent Application No. 10-2011-0131115, filed on Dec. 8, 2011, and Korean Patent Application No. 10-2012-0142241, filed on Dec. 7, 2012, in the Korean Intellectual Property Office, the disclosure of which is incorporated herein by reference in its entirety.

BACKGROUND

1. Field

Example embodiments relate to photorefractive composites, spatial light modulators, and hologram display devices using the same.

2. Description of the Related Art

In order to realize holograms, studies have been actively conducted about a spatial light modulator (SLM) that uses a photorefractive composite. The photorefractive composite is a material simultaneously having optical nonlinearity and photoconductivity, and a refractive index of which is periodically spatially modulated (spatial modulation of refractive index) due to redistribution of charges generated by light irradiation. The SLM is an apparatus that may modulate intensity and a phase of a light beam, and may repeatedly record 3D information. However, current SLMs do not have a sufficient modulation speed to realize a display. Therefore, there is a need to develop a new photorefractive composite.

SUMMARY

Example embodiments relate to photorefractive composites, spatial light modulators, and hologram display devices using the same.

Provided are photorefractive composites having increased photorefractive effect and photorefractive speed.

Provided are spatial light modulators (SLMs) having increased optical modulation effect and optical modulation speed.

Provided are hologram display devices having increased image transformation speed.

According to example embodiments, there is provided a photorefractive composite including at least one carborane compound expressed as the following Chemical Formulae 1A through 1C:

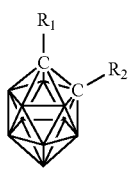

<Chemical Formula 1A>

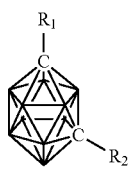

<Chemical Formula 1B>

<Chemical Formula 1C>

In the above Chemical Formulae 1A through 1C, $R_1$ and $R_2$ may be, independently from each other, one selected from hydrogen atoms, deuterium atoms, halogen atoms, substituted or non-substituted $C_1$-$C_{30}$ alkyl groups, substituted or non-substituted $C_2$-$C_{30}$ alkenyl groups, substituted or non-substituted $C_2$-$C_{30}$ alkynyl groups, substituted or non-substituted $C_1$-$C_{30}$ alkoxy groups, substituted or non-substituted $C_3$-$C_{30}$ cycloalkyl groups, substituted or non-substituted $C_3$-$C_{30}$ cycloalkenyl groups, substituted or non-substituted $C_5$-$C_{30}$ aryl groups, substituted or non-substituted $C_2$-$C_{30}$ heteroaryl groups, substituted or non-substituted $C_5$-$C_{30}$ aryloxy groups, and substituted or non-substituted $C_5$-$C_{30}$ aryltio groups. The photorefractive composite exhibits photoconductivity and optical nonlinearity.

In example embodiments, the at least one carborane compound may be at least one compound expressed as the following Chemical Formulae 2A through 2M:

Chemical Formula 2A

Chemical Formula 2B

Chemical Formula 2C

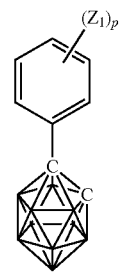

Chemical Formula 2D

Chemical Formula 2E

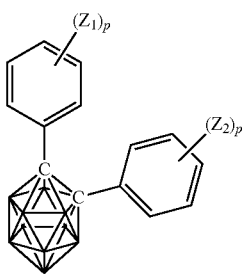

Chemical Formula 2F

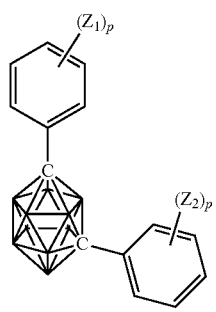

Chemical Formula 2G

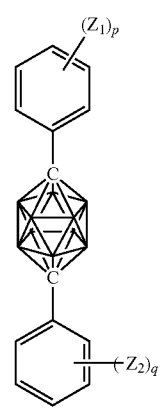

Chemical Formula 2H

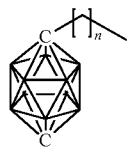

Chemical Formula 2I

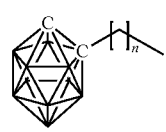

Chemical Formula 2J

Chemical Formula 2K

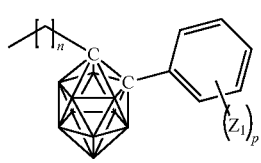

Chemical Formula 2L

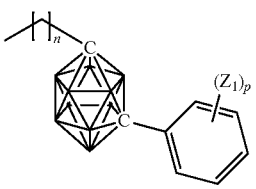

Chemical Formula 2M

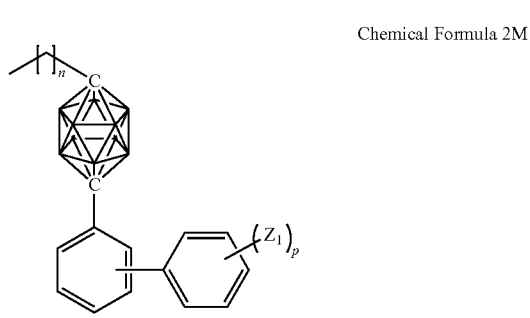

where, $Z_1$ and $Z_2$ are, independently from each other, one selected from hydrogen atoms, deuterium atoms, halogen atoms, substituted or non-substituted $C_1$-$C_{20}$ alkyl groups, substituted or non-substituted $C_2$-$C_{20}$ alkenyl groups, substituted or non-substituted $C_2$-$C_{20}$ alkynyl groups, substituted or non-substituted $C_1$-$C_{20}$ alkoxy groups, substituted or non-substituted $C_3$-$C_{20}$ cycloalkyl groups, substituted or non-substituted $C_3$-$C_{20}$ cycloalkenyl groups, substituted or non-substituted $C_5$-$C_{20}$ aryl groups, substituted or non-substituted $C_2$-$C_{20}$ heteroaryl groups, substituted or non-substituted $C_5$-$C_{20}$ aryloxy groups, and substituted or non-substituted $C_5$-$C_{20}$ aryltio groups, where $Z_1$ and $Z_2$ are the same or different, p and q are integers of 1 through 5, and n is an integer of 0 through 10.

In example embodiments, the substituted C5-C60 aryl groups may include at least one carborane group. The at least one carborane compound may be at least one compound expressed as the following Chemical Formulae 2N through 2P:

Chemical Formula 2N

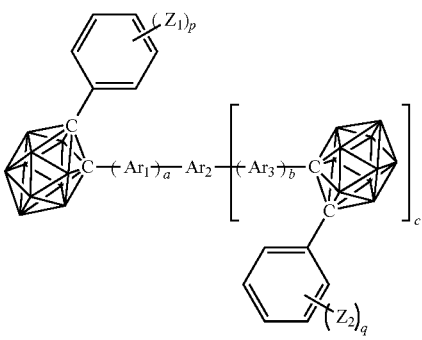

Chemical Formula 2O

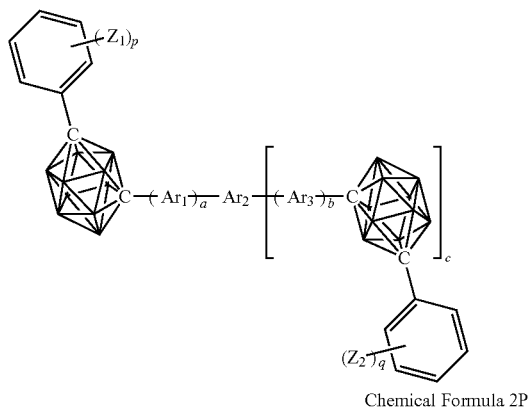

Chemical Formula 2P

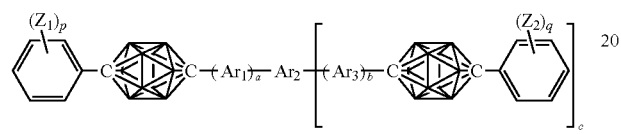

where, $Z_1$ and $Z_2$ are, independently from each other, one selected from hydrogen atoms, deuterium atoms, halogen atoms, substituted or non-substituted C1-C20 alkyl groups, substituted or non-substituted C2-C20 alkenyl groups, substituted or non-substituted C2-C20 alkynyl groups, substituted or non-substituted C1-C20 alkoxy groups, substituted or non-substituted C3-C20 cycloalkyl groups, substituted or non-substituted C3-C20 cycloalkenyl groups, substituted or non-substituted C5-C20 aryl groups, substituted or non-substituted C2-C20 heteroaryl groups, substituted or non-substituted C5-C20 aryloxy groups, and substituted or non-substituted C5-C20 aryltio groups, Z1 and Z2 are the same or different, p and q are integers of 1 through 5, n is an integer of 0 through 10, Ar1, Ar2, and Ar3 are, independently from each other, substituted or non-substituted C5-C20 arylene groups, a and b are integers of 0 to 2, and c is an integer of 1 to 5.

In example embodiments, the at least one carborane compound may be at least one compound expressed as the following Chemical Formulae 2A through 2C:

Chemical Formula 2A

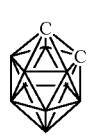

Chemical Formula 2B

Chemical Formula 2C

In example embodiments, the at least one carborane compound may be at least one compound expressed as the following Chemical Formulae 3A through 3D:

Chemical Formula 3A

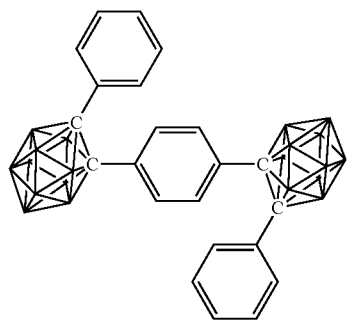

Chemical Formula 3B

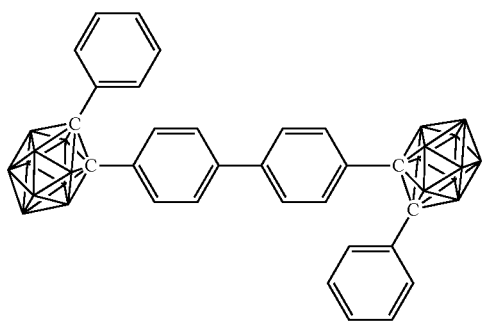

Chemical Formula 3C

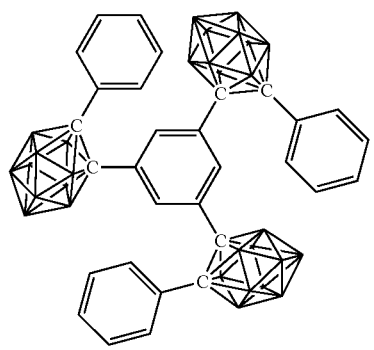

Chemical Formula 3D

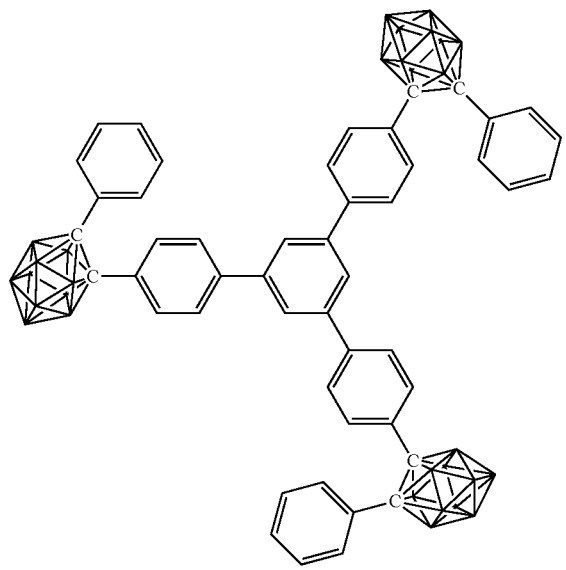

In example embodiments, the at least one carborane compound may be present in the photorefractive composite in an amount of about 0.1 parts to about 5 parts by weight with respect to 100 parts by weight of the photorefractive composite.

In example embodiments, the photorefractive composite may include a photoconductive polymer, wherein the photoconductive polymer may be one selected from the group consisting of polyvinylcarbazole (PVK), polysiloxane carbazole, polyparaphenylenevinylene, polyaniline, polypyrrole, polyacetylene, polythiophene, polyalkylthiophene, poly(alkylthiophene), carbazole-substituted polysiloxane (PSX-Cz), poly(p-phenylene terephthalate) carbazole (PPT-CZ), polyacrylate triphenylamine (TATPD), derivatives thereof, and a mixture of these materials.

In example embodiments, the photoconductive polymer may be present in the photorefractive composite in an amount of about 30 parts to about 60 parts by weight with respect to 100 parts by weight of the photorefractive composite.

In example embodiments, the photorefractive composite may include a nonlinear optical chromophore, wherein the nonlinear optical chromophore may be one selected from the group consisting of 4-piperidinobenzylidene malononitrile (PDCST), 2,5-dimethyl-4-(p-nitrophenylazo)anisole (DMNPAA), 2,N,N-dihexyl-amino-7-dicyanomethylidenyl-3,4,5,6,10-pentahydronaphthalene (DHADC-MPN), 4-di(2-methoxyethyl)aminobenzylidene malonotitrile (AODCST), amino-thienyl-dioxocyano-pyridine (ATOP), fluorinated cyano-tolane chromophore (FTCN), diethylamino-nitrostyrene (DEANST), and a mixture of these materials.

In example embodiments, the nonlinear optical chromophore may be present in the photorefractive composite in an amount of about 20 parts to about 50 parts by weight with respect to 100 parts by weight of the photorefractive composite.

In example embodiments, the photorefractive composite may further include a photosensitizer. The photosensitizer may be one selected from the group consisting of $C_{60}$ fullerene, phenyl-$C_{61}$-butyric acid methyl ester (PCBM), 2,4,7-trinitrofluorenone (TNF), 2,4,7-trinitro-9-fluorenylidene-malononitrile (TNFDM), and a mixture of these materials. The photosensitizer may be present in the photorefractive composite in an amount of about 0.1 parts to 3 about parts by weight with respect to 100 parts by weight of the photorefractive composite. The photosensitizer may be excitable by a light source having a wavelength in a range of about 380 nm to about 740 nm.

In example embodiments, the photorefractive composite may further include a plasticizer. The plasticizer may be one selected from the group consisting of ethylcarbazole (ECZ), dimethyl phthalate (DMP), diethyl phthalate (DEP), diisobutyl phtalate (DIBP), dibutyl phtalate (DBP), diheptylphtalate (DHP), di-2-ethylhexyl phthalate (DOP), dioctyl phthalate (DIOP), di-n-octyl phthalate (DnOP), dinonyl phthalate (DNP), diisodecyl phthalate (DIDP), ditridecyl phthalate (DTDP), dicyclohexyl phthalate (DCHP), benzyl butyl phthalate (BBP), butyl lauryl phthalate (BLP), dioctyl adipate (DOA), diisodecyl adipate (DIDA), dioctyl azelate (DOZ), dibutyl sebacate (DBS), dioctyl sebacate (DOS), dioctyl terephthalate (DOTP), diethylene glycol dibenzoate (DEDB), butyl oleate (BO), tricresyl phosphate (TCP), trioctyl phosphate (TOP), triphenyl phosphate (TPP), trichloroethyl phosphate (TCEP), and a mixture of these materials. The plasticizer may be present in the photorefractive composite in an amount of about 1 part to 20 parts by weight with respect to 100 parts by weight of the photorefractive composite.

In example embodiments, an electric conductivity of the photoconductive polymer may increase when the photoconductive polymer absorbs electromagnetic radiation.

In example embodiments, a light absorption region of the at least one carborane compound may be in a visible light region, and the photorefractive composite may exclude additional photosensitizers.

According to example embodiments, there is provided a spatial light modulator (SLM) that includes a first electrode, a second electrode corresponding to the first electrode, and a photorefractive layer between the first and second electrodes, wherein the photorefractive layer includes at least one carborane compound expressed as the above Chemical Formulae 1A through 1C, and the photorefractive layer exhibits photoconductivity and optical nonlinearity.

In example embodiments, the at least one carborane compound may be at least one selected from the group consisting of compounds expressed as the following Chemical Formulae 2A through 2M:

Chemical Formula 2A

Chemical Formula 2B

Chemical Formula 2C

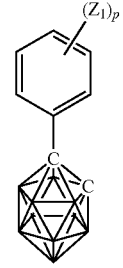

Chemical Formula 2D

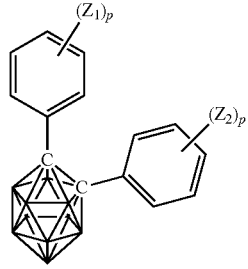

Chemical Formula 2E

Chemical Formula 2F

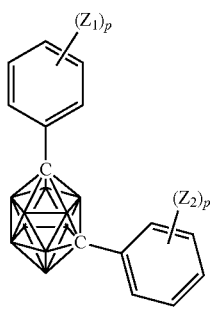

Chemical Formula 2G

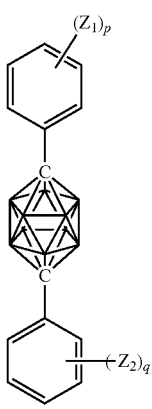

Chemical Formula 2H

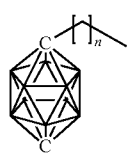

Chemical Formula 2I

Chemical Formula 2J

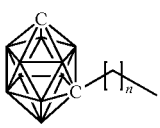

Chemical Formula 2K

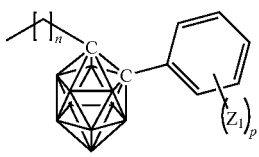

Chemical Formula 2L

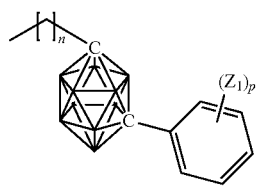

Chemical Formula 2M

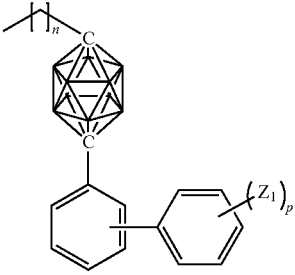

where, $Z_1$ and $Z_2$ are, independently from each other, one selected from hydrogen atoms, deuterium atoms, halogen atoms, substituted or non-substituted $C_1$-$C_{20}$ alkyl groups, substituted or non-substituted $C_2$-$C_{20}$ alkenyl groups, substituted or non-substituted $C_2$-$C_{20}$ alkynyl groups, substituted or non-substituted $C_1$-$C_{20}$ alkoxy groups, substituted or non-substituted $C_3$-$C_{20}$ cycloalkyl groups, substituted or non-substituted C3-C20 cycloalkenyl groups, substituted or non-substituted C5-C20 aryl groups, substituted or non-substituted C2-C20 heteroaryl groups, substituted or non-substituted C5-C20 aryloxy groups, and substituted or non-substituted C5-C20 aryltio groups, Z1 and Z2 are the same or different, p and q are integers of 1 through 5, and n is an integer of 0 through 10. In example embodiments, the substituted C5-C60 aryl groups may include at least one carborane group. The at least one carborane compound may be at least one compound expressed as the following Chemical Formulae 2N through 2P:

Chemical Formula 2N

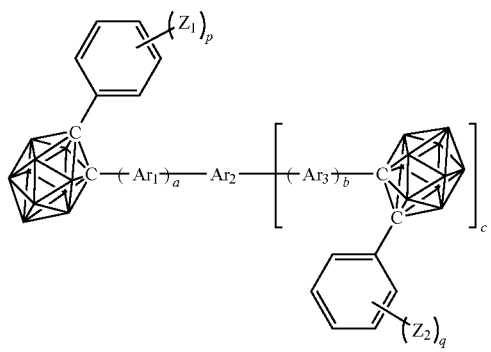

Chemical Formula 2O

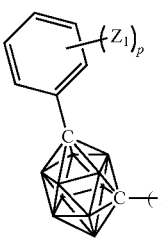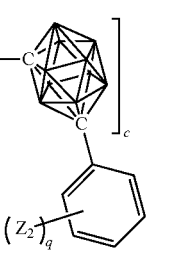

Chemical Formula 2P

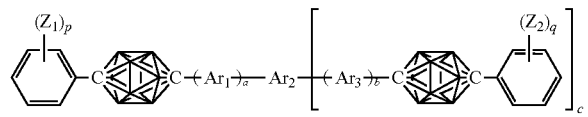

where, $Z_1$ and $Z_2$ are, independently from each other, one selected from hydrogen atoms, deuterium atoms, halogen atoms, substituted or non-substituted $C_1$-$C_{20}$ alkyl groups, substituted or non-substituted $C_2$-$C_{20}$ alkenyl groups, substituted or non-substituted $C_2$-$C_{20}$ alkynyl groups, substituted or non-substituted $C_1$-$C_{20}$ alkoxy groups, substituted or non-substituted $C_3$-$C_{20}$ cycloalkyl groups, substituted or non-substituted $C_3$-$C_{20}$ cycloalkenyl groups, substituted or non-substituted $C_5$-$C_{20}$ aryl groups, substituted or non-substituted $C_2$-$C_{20}$ heteroaryl groups, substituted or non-substituted $C_5$-$C_{20}$ aryloxy groups, and substituted or non-substituted $C_5$-$C_{20}$ aryltio groups, $Z_1$ and $Z_2$ are the same or different, p and q are integers of 1 through 5, n is an integer of 0 through 10, Ar1, Ar2, and Ar3 are, independently from each other, substituted or non-substituted $C_5$-$C_{20}$ arylene groups, a and b are integers of 0 to 2, and c is an integer of 1 to 5.

In example embodiments, the at least one carborane compound may be one of the compounds expressed as the following Chemical Formulae 2A through 2C:

Chemical Formula 2A

Chemical Formula 2B

Chemical Formula 2C

In example embodiments, the SLM may include a photoconductive polymer, wherein the photoconductive polymer may be one selected from the group consisting of polyvinylcarbazole (PVK), polysiloxane carbazole, polyparaphenylenevinylene, polyaniline, polypyrrole, polyacetylene, polythiophene, polyalkylthiophene, poly(alkylthiophene), carbazole-substituted polysiloxane (PSX-Cz), poly(p-phenylene terephthalate) carbazole (PPT-CZ), polyacrylate triphenylamine (TATPD), derivatives thereof, and a mixture of these materials.

In example embodiments, the SLM may include a nonlinear optical chromophore, wherein the nonlinear optical chromophore may be one selected from the group consisting of 4-piperidinobenzylidene malononitrile (PDCST), 2,5-dimethyl-4-(p-nitrophenylazo)anisole (DMNPAA), 2,N,N-dihexyl-amino-7-dicyanomethylidenyl-3,4,5,6,10-pentahydronaphthalene (DHADC-MPN), 4-di(2-methoxyethyl) aminobenzylidene malonotitrile (AODCST), amino-thienyl-dioxocyano-pyridine (ATOP), fluorinated cyano-tolane chromophore (FTCN), and diethylamino-nitrostyrene (DEANST), and a mixture of these materials.

In example embodiments, the SLM may further include a photosensitizer. The photosensitizer may be excitable by a light source having a wavelength in a range of about 380 nm to about 740 nm. The photosensitizer may be one selected from the group consisting of C60 fullerene, phenyl-C61-butyric acid methyl ester (PCBM), 2,4,7-trinitrofluorenone (TNF), and 2,4,7-trinitro-9-fluorenylidene-malononitrile (TNFDM), and a mixture of these materials.

In example embodiments, the SLM may further include a plasticizer. The plasticizer may be one selected from the group consisting of ethylcarbazole (ECZ), dimethyl phthalate (DMP), diethyl phthalate (DEP), diisobutyl phtalate (DIBP), dibutyl phtalate (DBP), diheptylphtalate (DHP), di-2-ethylhexyl phthalate (DOP), dioctyl phthalate (DIOP), di-n-octyl phthalate (DnOP), dinonyl phthalate (DNP), diisodecyl phthalate (DIDP), ditridecyl phthalate (DTDP), dicyclohexyl phthalate (DCHP), benzyl butyl phthalate (BBP), butyl lauryl phthalate (BLP), dioctyl adipate (DOA), diisodecyl adipate (DIDA), dioctyl azelate (DOZ), dibutyl sebacate (DBS), dioctyl sebacate (DOS), dioctyl terephthalate (DOTP), diethylene glycol dibenzoate (DEDB), butyl oleate (BO), tricresyl phosphate (TCP), trioctyl phosphate (TOP), triphenyl phosphate (TPP), trichloroethyl phosphate (TCEP) and a mixture of these materials.

In example embodiments, an electric conductivity of the photoconductive polymer may increase when the photoconductive polymer absorbs electromagnetic radiation.

In example embodiments, a light absorption region of the at least one carborane compound may be in a visible light region, and the photorefractive composite may exclude additional photosensitizers.

According to example embodiments, there is provided a hologram display device including a light source unit configured to irradiate light for recording and reproducing a three-dimensional image of an object, an input unit configured to input three-dimensional image information of the object, a display unit that includes the spatial light modulator (SLM) wherein the display unit is configured to record three-dimensional image information of the object input by the input unit and is configured to reproduce the three-dimensional image of the object using the light irradiated from the light source unit, and an optical system configured to transmit the light irradiated from the light source unit to the input unit and the display unit.

A carborane compound that may spatially fix electrons is included in the photorefractive composite, and thus, the photorefractive speed of the photorefractive composite may be increased. Also, a spatial light modulator (SLM) having an increased light modulation speed and a hologram display device having an increased image transformation speed may be provided by using a photorefractive composite having an increased photorefractive speed.

BRIEF DESCRIPTION OF THE DRAWINGS

Example embodiments will be more clearly understood from the following detailed description taken in conjunction with the accompanying drawings.

FIG. 1 is a schematic cross-sectional view of a spatial light modulator (SLM) according to example embodiments;

FIG. 2 is a schematic cross-sectional view of a hologram display device according to example embodiments;

FIG. 3 is a graph of an electric field versus dark conductivity of photorefractive devices according to example embodiments and a comparative example; and FIG. 4 is a graph of an electric field versus photo conductivity of photorefractive devices according to example embodiments and a comparative example.

DETAILED DESCRIPTION

Figure 1:
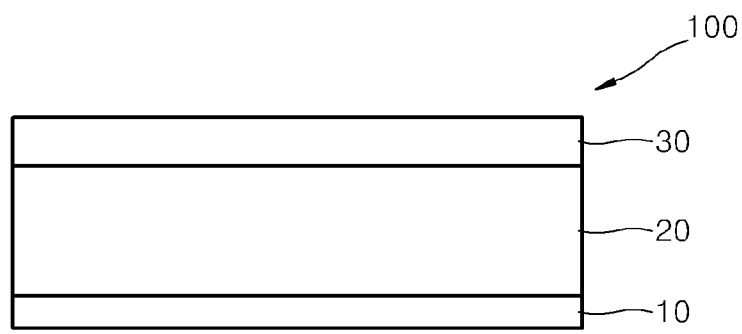
FIGS. 1-4 represent non-limiting, example embodiments as described herein.

Various example embodiments will now be described more fully with reference to the accompanying drawings in which some example embodiments are shown. However, specific structural and functional details disclosed herein are merely representative for purposes of describing example embodiments, and thus may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope of the disclosure.

In the drawings, the thicknesses of layers and regions may be exaggerated for clarity, and like numbers refer to like elements throughout the description of the figures.

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that, if an element is referred to as being "connected" or "coupled" to another element, it can be directly connected, or coupled, to the other element or intervening elements may be present. In contrast, if an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," if used herein, specify the presence of stated features, integers, steps, operations, elements and/or components, but do not preclude the presence or addition of one or more other features, integers, steps, operations, elements, components and/or groups thereof.

Spatially relative terms (e.g., "beneath," "below," "lower," "above," "upper" and the like) may be used herein for ease of description to describe one element or a relationship between a feature and another element or feature as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, for example, the term "below" can encompass both an orientation that is above, as well as, below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments relate to photorefractive composites, spatial light modulators, and hologram display devices using the same.

A photorefractive composite according to example embodiments includes a photoconductive polymer, a nonlinear optical chromophore, and a carborane compound.

The photoconductive polymer is a kind of polymer, the electric conductivity of which is increased when it absorbs electromagnetic radiation. The electromagnetic radiation includes light (e.g., visible light, ultraviolet rays, and infrared rays). The photoconductive polymer changes a spatial ratio between electrons and holes by moving charges generated in a photorefractive composite due to the light irradiation, and thus, may induce an electric field in the photorefractive composite.

The photoconductive polymer may include, for example, a carbazole unit or a triphenyl amine unit, but is not limited thereto. The photoconductive polymer may include polyvinylcarbazole (PVK), polysiloxane carbazole, polyparaphenylenevinylene, polyaniline, polypyrrole, polyacetylene, polythiophene, poly(alkylthiophene), carbazole-substituted polysiloxane (PSX-Cz), poly(p-phenylene terephthalate) carbazole (PPT-CZ), polyacrylate triphenylamine (TATPD), derivatives thereof, a mixture of these materials, or a copolymer of these materials.

The content of the photoconductive polymer in a photorefractive composite may be in a range between 30 parts and 60 parts by weight based on 100 parts by weight of the photorefractive composite.

The nonlinear optical chromophores generate a difference of spatial refractive index by an electric field induced in a photorefractive composite.

The nonlinear optical chromophore may include, for example, 4-piperidinobenzylidene malononitrile (PDCST), 2,5-dimethyl-4-(p-nitrophenylazo)anisole (DMNPAA), 2, N,N-dihexyl-amino-7-dicyanomethylidenyl-3,4,5,6,10-pentahydronaphthalene (DHADC-MPN), 4-di(2-methoxyethyl) aminobenzylidene malonotitrile (AODCST), amino-thienyl-dioxocyano-pyridine (ATOP), fluorinated cyano-tolane chromophore (FTCN), or diethylamino-nitrostyrene (DEANST).

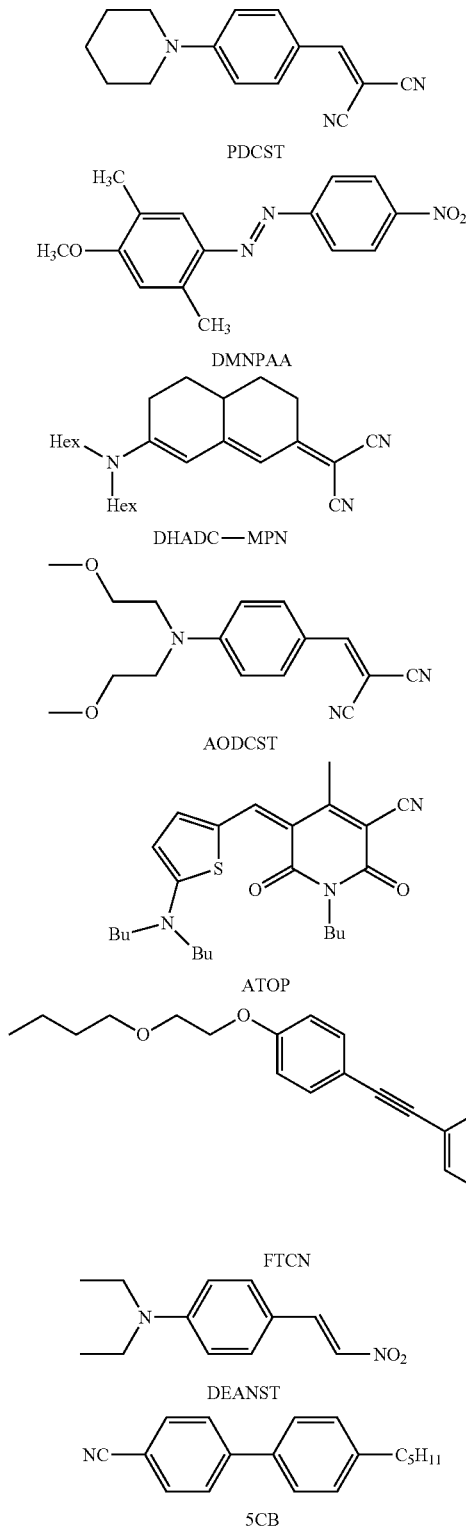

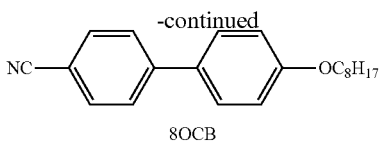

8OCB

The nonlinear optical chromophore in a photorefractive composite may be in a range from about 20 parts to about 50 parts by weight with respect to 100 parts by weight of the photorefractive composite.

A carborane compound that includes a plurality of boron, which is an electron-deficient atom, has high electron affinity. Thus, a carborane compound may readily trap electrons. A difference of spatial distribution of holes and electrons are generated in a photorefractive composite when electrons are well trapped in the photorefractive composite, and accordingly, photorefractive modulation speed may be increased, and also, a photorefractive effect may be increased due to the reduction of a dark current.

A carborane compound may absorb light, and a wavelength region of light to be absorbed may be controlled by controlling a conjugation length of the carborane compound. The conjugation length of a carborane compound may be controlled by changing a substitution group. For example, when a conjugation length of a substitution group is increased, a light absorption region of a carborane compound may be in a visible light region. When a light absorption region of a carborane compound is in a visible light region, an additional photosensitizer may not be used in the photorefractive composite because the carborane compound may function as a photosensitizer that generates charges in a photorefractive composite.

The carborane compound may be one of the compounds expressed as Chemical Formulae 1A through 1C.

<Chemical Formula 1A>

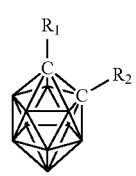

<Chemical Formula 1B>

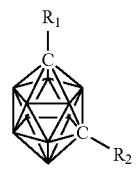

<Chemical Formula 1C>

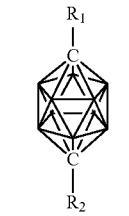

In the Chemical Formulae 1A through 1C, $R_1$ and $R_2$ may be, independently from each other, hydrogen atoms, deuterium atoms, halogen atoms, substituted or non-substituted $C_1$-$C_{30}$ alkyl groups, substituted or non-substituted $C_2$-$C_{30}$ alkenyl groups, substituted or non-substituted $C_2$-$C_{30}$ alkynyl groups, substituted or non-substituted $C_1$-$C_{30}$ alkoxy groups, substituted or non-substituted $C_3$-$C_{30}$ cycloalkyl groups, substituted or non-substituted $C_3$-$C_{30}$ cycloalkenyl groups, substituted or non-substituted $C_5$-$C_{60}$ aryl groups, substituted or non-substituted $C_2$-$C_{30}$ heteroaryl groups, substituted or non-substituted $C_5$-$C_{30}$ aryloxy groups, or substituted or non-substituted $C_5$-$C_{30}$ aryltio groups. The substituted $C_5$-$C_{60}$ aryl groups may contain at least one carborane group or may not contain carborane group.

The terminology "substituted A" in the expression of "substituted or non-substituted A (A is an arbitrary substitution group)" denotes that at least one hydrogen atom in A is substituted by a group expressed as a deuterium atom, a halogen atom, a hydroxyl group, a cyano group, a nitro group, an amino group, a hydrazine, a hydrazone, a carboxyl group or a derivative of a salt thereof, a sulfonic acid group or a derivative of a sulfonate, a phosphoric acid group or a derivative of a phosphate, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_3$-$C_{20}$ cycloalkyl group, a $C_3$-$C_{20}$ cycloalkenyl group, a $C_5$-$C_{20}$ aryl group, a $C_5$-$C_{20}$ aryloxy group, a $C_5$-$C_{20}$ aryltio group, a $C_3$-$C_{20}$ heteroaryl group, a group expressed as $N(Q_1)(Q_2)$, and a group expressed as $Si(Q_3)(Q_4)(Q_5)$. Here, the $Q_1$ through $Q_5$ may be, independently from each other, hydrogen atoms, deuterium atoms, halogen atoms, hydroxyl groups, cyano groups, amino groups, nitro groups, carboxyl groups, $C_1$-$C_{20}$ alkyl groups, $C_2$-$C_{20}$ alkenyl groups, $C_2$-$C_{20}$ alkynyl groups, $C_1$-$C_{20}$ alkoxy groups, $C_3$-$C_{20}$ cycloalkyl groups, $C_3$-$C_{20}$ cycloalkenyl groups, $C_5$-$C_{20}$ aryl groups, $C_5$-$C_{20}$ aryloxy groups, or $C_5$-$C_{30}$ aryltio groups, or $C_2$-$C_{30}$ heteroaryl groups.

For example, the carborane compound may be one of the compounds expressed as Chemical Formulae 2A through 2P, but is not limited thereto.

<Chemical Formula 2A>

<Chemical Formula 2B>

<Chemical Formula 2C>

<Chemical Formula 2D>

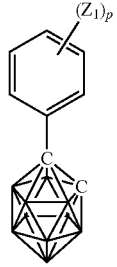

<Chemical Formula 2E>

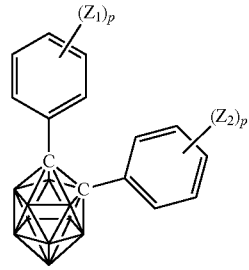

<Chemical Formula 2F>

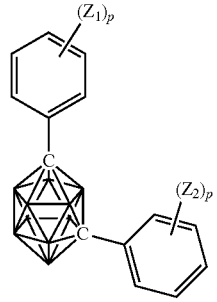

<Chemical Formula 2G>

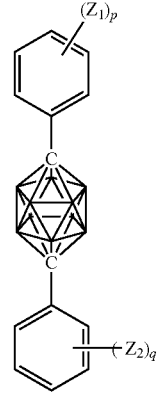

<Chemical Formula 2H>

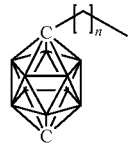

<Chemical Formula 2I>

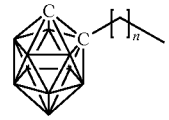

<Chemical Formula 2J>

<Chemical Formula 2K>

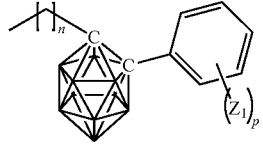

<Chemical Formula 2L>

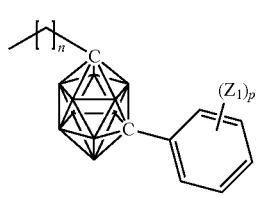

<Chemical Formula 2M>

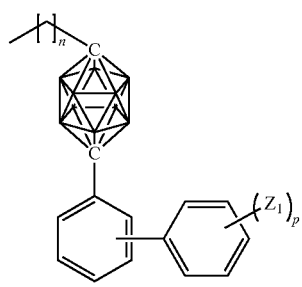

<Chemical Formula 2N>

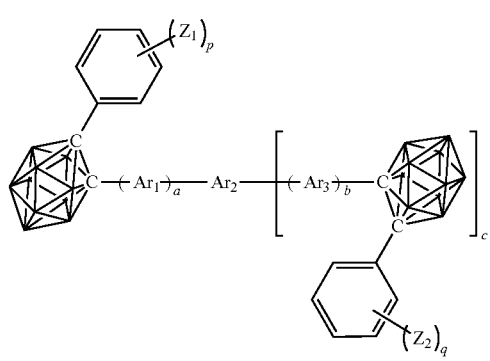

<Chemical Formula 2O>

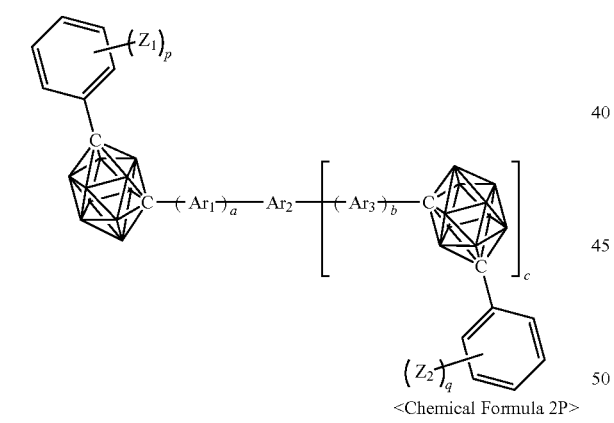

<Chemical Formula 2P>

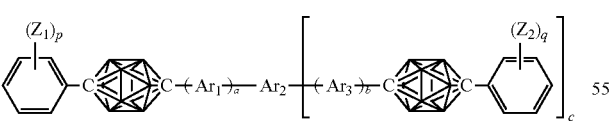

In the Chemical Formulae 2A through 2P, $Z_1$ and $Z_2$ may be, independently from each other, hydrogen atoms, deuterium atoms, halogen atoms, substituted or non-substituted $C_1$-$C_{20}$ alkyl groups, substituted or non-substituted $C_2$-$C_{20}$ alkenyl groups, substituted or non-substituted $C_2$-$C_{20}$ alkynyl groups, substituted or non-substituted $C_1$-$C_{20}$ alkoxy groups, substituted or non-substituted $C_3$-$C_{20}$ cycloalkyl groups, substituted or non-substituted $C_3$-$C_{20}$ cycloalkenyl groups, substituted or non-substituted $C_5$-$C_{20}$ aryl groups, substituted or non-substituted $C_2$-$C_{20}$ heteroaryl groups, substituted or non-substituted $C_5$-$C_{20}$ aryloxy groups, or substituted or non-substituted $C_5$-$C_{20}$ aryltio groups.

The plural numbers of $Z_1$ and $Z_2$ may be the same or different, p and q are integers of 1 through 5, and n is an integer of 0 through 10.

Ar1, Ar2, and Ar3 may be, independently from each other, substituted or non-substituted $C_5$-$C_{20}$ arylene groups, a and b may be integers of 0 to 2, and c may be an integer of 1 to 5.

More specifically, the carborane compound may be one of the compounds expressed as Chemical Formulae of 2A through 2C, but is not limited thereto.

<Chemical Formula 2A>

<Chemical Formula 2B>

<Chemical Formula 2C>

Also, the carborane compound may be one of the compounds expressed as Chemical Formulae of 3A through 3C, but is not limited thereto.

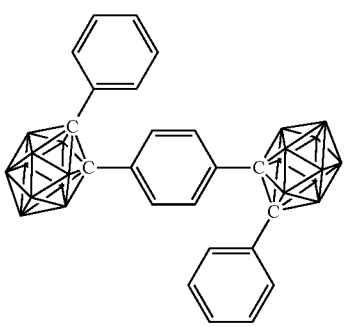

Chemical Formula 3A

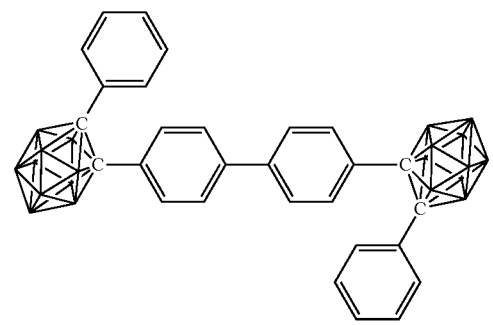

Chemical Formula 3B

-continued

Chemical Formula 3C

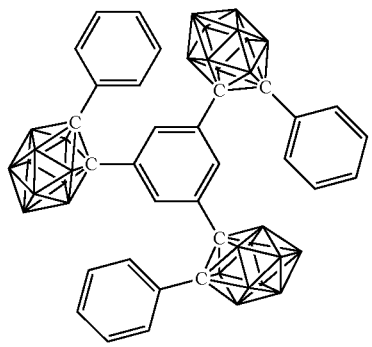

Chemical Formula 3D

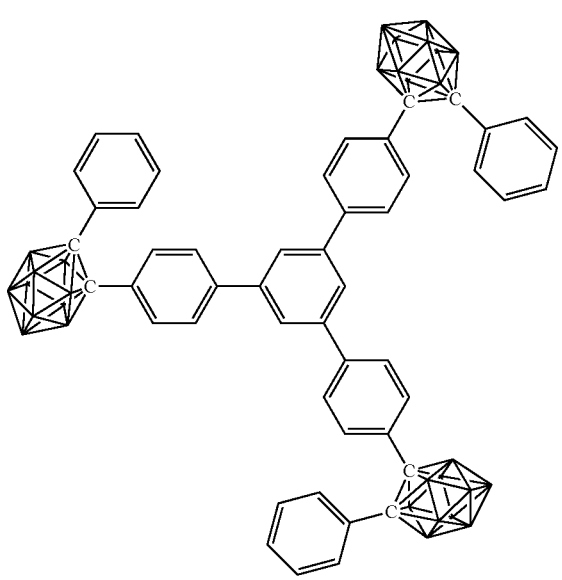

The content of the carborane compound in a photorefractive composite may be in a range from 0.1 parts to about 5 parts by weight with respect to 100 parts by weight of the photorefractive composite.

A photorefractive composite according to example embodiments may include a photoconductive polymer, a nonlinear optical chromophore, a carborane compound, and a photosensitizer.

The photoconductive polymer, the nonlinear optical chromophore, and the carborane compound are as described above, and thus, descriptions thereof are not repeated.

The photosensitizer may generate electrons and holes by being excited by a light source having a specific wavelength, for example, visible light. The photosensitizer may be, for example, $C_{60}$ fullerene, phenyl-$C_{61}$-butyric acid methyl ester (PCBM), 2,4,7-trinitrofluorenone (TNF), or 2,4,7-trinitro-9-fluorenylidene-malononitrile (TNFDM).

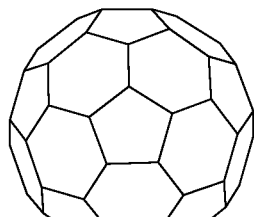

<$C_{60}$ fullerene>

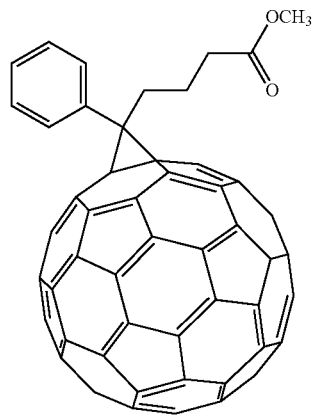

<PCBM>

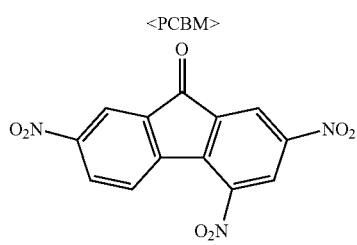

<TNF>

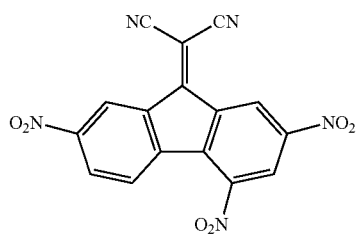

<TNFDM>

In the example embodiments, the photoconductive polymer may be included in a photorefractive composite in a range from about 20 parts to about 50 parts by weight with respect to 100 parts by weight of the total photorefractive composite. The nonlinear optical chromophore may be included in a photorefractive composite in a range from about 20 parts to about 50 parts by weight with respect to 100 parts by weight of the total photorefractive composite. The carborane compound may be included in a photorefractive composite in a range from about 0.1 parts to about 5 parts by weight with respect to 100 parts by weight of the total photorefractive composite. The photosensitizer may be included in a photorefractive composite in a range from about 0.1 parts to about 3 parts by weight with respect to 100 parts by weight of the total photorefractive composite.

A photorefractive composite according to other example embodiments may include a photoconductive polymer, a nonlinear optical chromophore, a carborane compound, a photosensitizer, and a plasticizer.

The photoconductive polymer, the nonlinear optical chromophore, the carborane compound, and the photosensitizer are as described above, and thus, descriptions thereof are not repeated.

The plasticizer increases the degree of freedom of materials of a photorefractive composite by reducing a glass transition temperature of the photorefractive composite. Thereby, the plasticizer increases an orientational enhancement effect of the photorefractive composite. Accordingly, the photorefractive efficiency of the photorefractive composite increases due to the orientational enhancement effect.

The plasticizer may be ethylcarbazole (ECZ), dimethyl phthalate (DMP), diethyl phthalate (DEP), diisobutyl phtalate (DIBP), dibutyl phtalate (DBP), diheptylphtalate (DHP), di-2-ethylhexyl phthalate (DOP), dioctyl phthalate (DIOP), di-n-octyl phthalate (DnOP), dinonyl phthalate (DNP), diisodecyl phthalate (DIDP), ditridecyl phthalate (DTDP), dicyclohexyl phthalate (DCHP), benzyl butyl phthalate (BBP), butyl lauryl phthalate (BLP), dioctyl adipate (DOA), diisodecyl adipate (DIDA), dioctyl azelate (DOZ), dibutyl sebacate (DBS), dioctyl sebacate (DOS), dioctyl terephthalate (DOTP), diethylene glycol dibenzoate (DEDB), butyl oleate (BO), tricresyl phosphate (TCP), trioctyl phosphate (TOP), triphenyl phosphate (TPP), trichloroethyl phosphate (TCEP) or a mixture of these materials.

In example embodiments, the photoconductive polymer may be included in a photorefractive composite in a range from about 30 parts to about 60 parts by weight with respect to 100 parts by weight of the total photorefractive composite. The nonlinear optical chromophore may be included in a photorefractive composite in a range from about 20 parts to about 50 parts by weight with respect to 100 parts by weight of the total photorefractive composite. The carborane compound may be included in a photorefractive composite in a range from about 0.1 parts to about 5 parts by weight with respect to 100 parts by weight of the total photorefractive composite. The photosensitizer may be included in a photorefractive composite in a range from about 0.1 parts to about 3 parts by weight with respect to 100 parts by weight of the total photorefractive composite. The plasticizer may be included in a photorefractive composite in a range from about 1 part to about 30 parts by weight with respect to 100 parts by weight of the total photorefractive composite.

Hereinafter, a space light modulator (SLM) according to example embodiments will now be described.

FIG. 1 is a schematic cross-sectional view of an SLM according to example embodiments.

Referring to FIG. 1, an SLM 100 may include a first electrode 10, a second electrode 30 facing the first electrode 10, and a photorefractive layer 20 interposed between the first electrode 10 and the second electrode 30. The first electrode 10 may be formed of a material including Au, Al, ITO, or IZO, but is not limited thereto. The second electrode 30 may be formed of the same material used to form the first electrode 10.

As described in the previous example embodiments, the photorefractive layer 20 may be formed of a photorefractive composite that includes a photoconductive polymer, a nonlinear optical chromophore, and a carborane compound.

When coherent light having the same wavelength is irradiated onto the photorefractive layer 20, charges are generated at a portion where constructive interference occurs. Thus, an internal electric field is generated by the charges. The internal electric field changes a refractive index of the photorefractive layer 20, and a diffraction grating structure is formed in the photorefractive layer 20. The diffraction grating formed in an SLM has three-dimensional image information. Thus, when a reference beam is irradiated onto the SLM, a three-dimensional image is displayed around the SLM.

In the example embodiments, the redistribution speed of charges according to the change of light irradiation is increased because a photorefractive composite having a carborane compound is used in the photorefractive layer 20. Thus, the photorefractive speed is increased, and accordingly, the light modulation speed is increased.

A hologram display device according to example embodiments will now be described.

Figure 2:
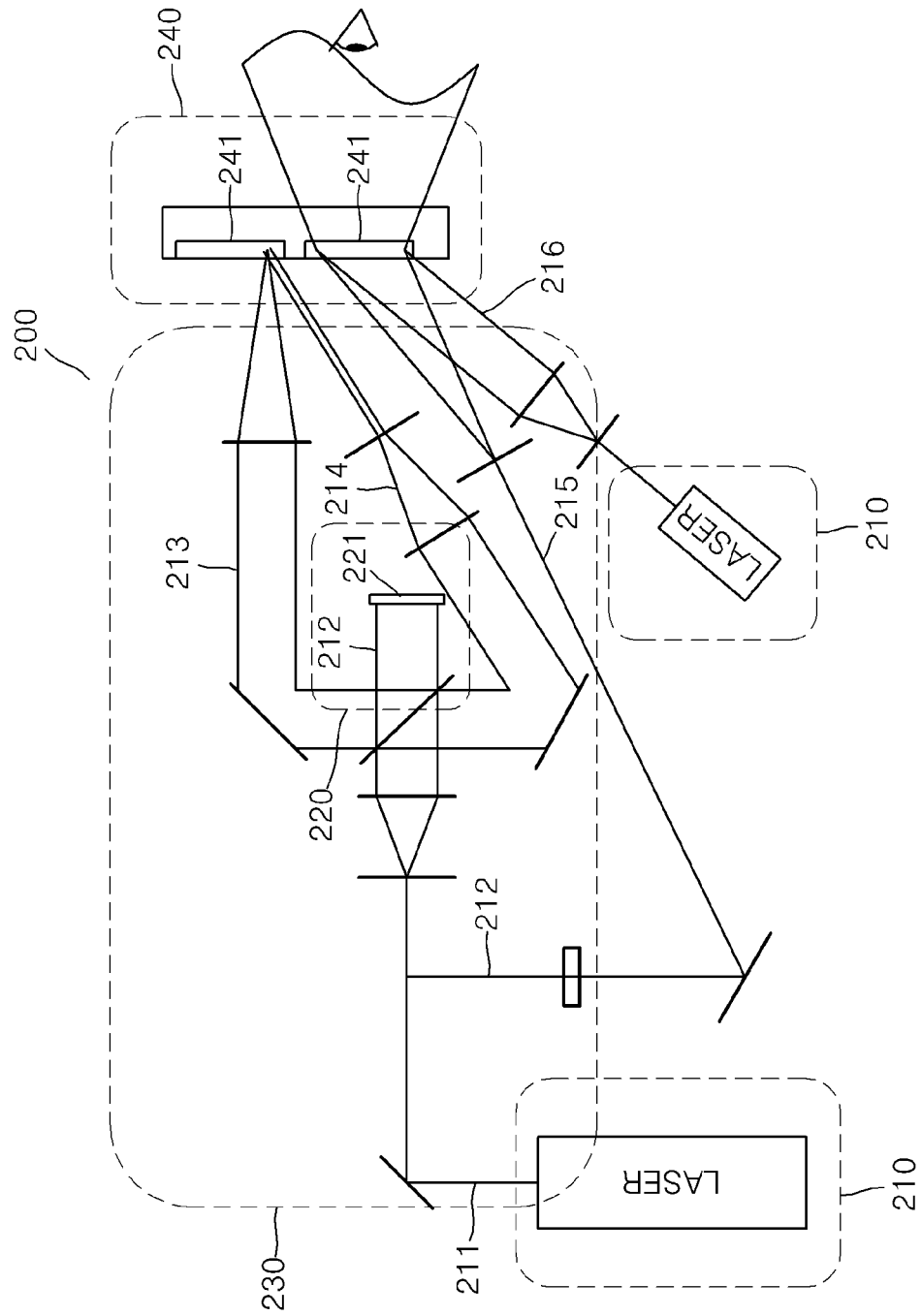

FIG. 2 is a schematic cross-sectional view of a hologram display device according to example embodiments.

Referring to FIG. 2, a hologram display device 200 may include a light source unit 210, an input unit 220, an optical system 230, and a display unit 240.

The light source unit 210 generates a laser beam to be used for providing, recording, and reproducing three-dimensional image information of an object in the input unit 220 and the display unit 240.

The input unit 220 inputs three-dimensional image information of an object to be recorded in the display unit 240 in advance. The input unit 220 may input, for example, three-dimensional image information of an object such as intensity and phase of light in each space to an electrically addressed liquid crystal SLM 221. At this point, an input beam 212 may be used.

The optical system 230 may include a mirror, a polarizer, a beam splitter, a beam shutter, and a lens. The optical system 230 may divide a laser beam 211 generated from the light source 210 into the input beam 212 sent to the input unit 220, a recording beam 213, a reference beam 214, an erasing beam 215, and a reading beam 216 that are transmitted to the display unit 240.

The display unit 240 may receive three-dimensional image information of an object from the input unit 220 and may record it in a hologram plate 241 configured by an optically addressed SLM, and may reproduce a three-dimensional image of the object. At this point, three-dimensional image information may be recorded through interference between the recording beam 213 and the reference beam 214. The optically addressed SLM of the hologram plate 241 may use the SLM 100 described above. Three-dimensional image information of an object recorded in the hologram plate 241 may be reproduced to a three-dimensional image by a diffraction pattern generated from the reading beam 216. The erasing beam 215 may be used for rapidly restoring the formed diffraction grating. Meanwhile, the hologram plate 241 may be moved to a location between an input point and a reproducing point of a three-dimensional image.

Because the SLM 100 described above is used in the optically addressed SLM of the hologram plate 241, the hologram display device 200 according to example embodiments may have an increased image modulation speed as a result of a rapid optical modulation speed.

Also, the photorefractive composite and the SLM 100 described above may be applied to the hologram display device 200 as well as various types of hologram display devices.

SYNTHESIS EXAMPLE

Chemical Formula 3B

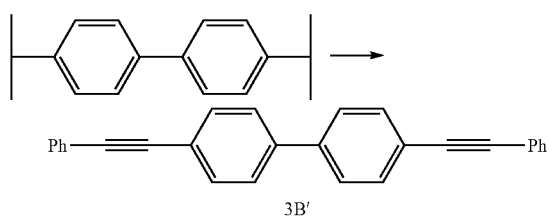

3B'

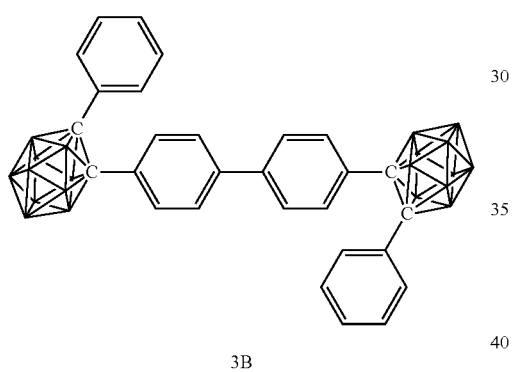

3B

Synthesis of Intermediate 3B'

2 g (4.9 mmol) of 4,4'-diiodobiphenyl, 80 mg of copper iodide and 120 mg of Pd(PPh$_3$)$_2$Cl$_2$ were mixed in 100 ml of toluene/triethylamine (1/9 volume ratio). 1.5 mL of phenylacetylene was added to the mixture, and then refluxed in 24 hours to generate a solid. The generated solid was filtered and washed with methanol to obtained 1.60 g (Yield: 92%) of Intermediate 3B'. The formed intermediate was confirmed by Element Analysis. Anal. Calcd for C28H18: C, 94.88; H, 5.12. Found: C, 94.92; H, 5.08.

Synthesis of Chemical Formula 3B 1.0 g (2.2 mmol) of Intermediate 3B' and 0.6 g (5.0 mmol) of decaborane was dissolved in 100 ml of toluene, and 5 equivalents of Et2S (diethyl sulfide) were added and mixtured in room temperature. The mixture was refluxed and stirred for 3 days. Methanol was added to generate a solid. The generated solid was filtered and recrystallized in n-hexane to obtain 0.73 g (Yield: 50%) of Chemical Formula 3B (yellow color).

The formed compound was confirmed by Element Analysis. Anal. Calcd for C28H38B20: C, 56.92; H, 6.48. Found: C, 55.89; H, 6.44.

SYNTHESIS EXAMPLE

Chemical Formula 3D

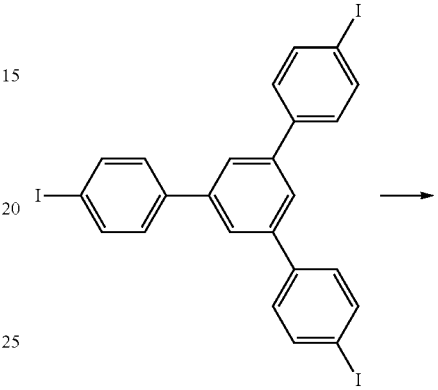

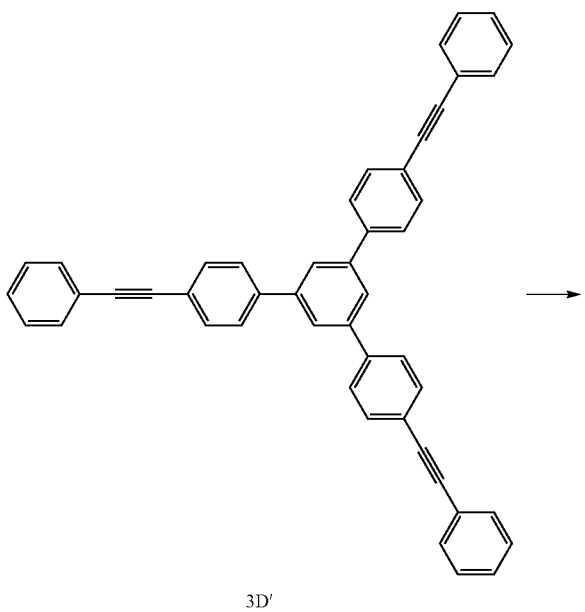

3D'

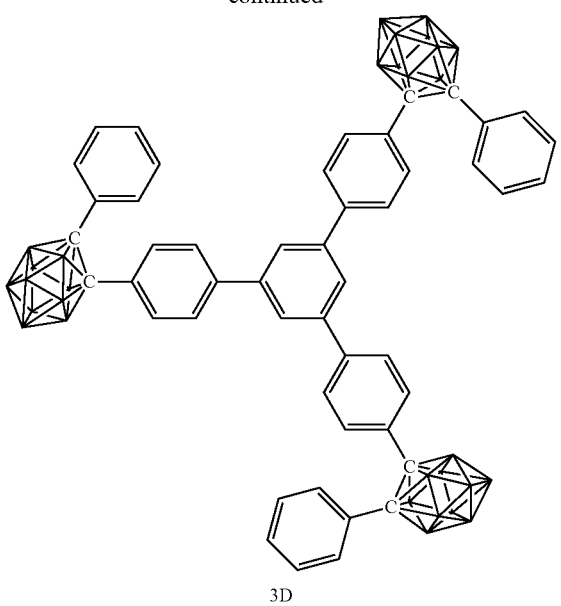

3D

Synthesis of Intermediate 3D'

Intermediate 3D' was prepared in the same manner as used to prepare Intermediate 3B' except that 4,4''-diiodo-5'-(4-iodophenyl)-1,1':3',1''-terphenyl was used instead of 4-diiodobiphenyl. The formed intermediate was confirmed by Element Analysis. Anal. Calcd for C48H30: C, 95.02; H, 4.98. Found: C, 94.99; H, 5.01.

Synthesis of Chemical Formula 3D

Chemical Formula 3D was prepared in the same manner as used to prepare Compound 3B except that Intermediate 3D' was used instead of Intermediate 3B'. The formed compound was confirmed by Element Analysis. Anal. Calcd for C48H60B30: C, 59.67; H, 6.29. Found: C, 59.62; H, 6.30.

EXAMPLE EMBODIMENT 1

A photorefractive composite solution was made by resolving PVK: PDCST: ECZ:PCBM: Chemical Formula 2A (o-carborane,Aldrich) with a weight ratio of 49.4: 30:20:0.5: 0.1 in a toluene solvent. At this point, a weight ratio of the total constituent (PVK: PDCST: ECZ: PCBM: Chemical Formula 2A (o-carborane, Aldrich)) with respect to the toluene solvent was 4:1.

The photorefractive composite solution was filled between two ITO electrodes separated 100 µm by a spacer. Afterwards, a photorefractive device having a photorefractive layer between the two electrodes was formed by removing the toluene solvent through evaporation.

EXAMPLE EMBODIMENT 2

A photorefractive device was formed by the same method of Example Embodiment 1 except that carborane compound of Chemical Formula 3B was used instead of o-carborane (Chemical Formula 2A).

EXAMPLE EMBODIMENT 3

A photorefractive device was formed by the same method of Example Embodiment 1 except that carborane compound of Chemical Formula 3D was used instead of o-carborane (Chemical Formula 2A).

COMPARATIVE EXAMPLE 1

A photorefractive device was formed through the same process used in the Example Embodiment 1 except for use of the carborane compound.

The ratio of compositions of the photorefractive composites of the Example Embodiments 1 and 2 and the Comparative Example 1 are summarized in Table 1.

TABLE 1

|  | photoconductive polymer | nonlinear optical chromophore | photosensitizer | plasticizer | Carborane compound |
|---|---|---|---|---|---|
| Embodiment 1 | PVK 49.4 wt % | PDCST 30 wt % | PCBM 0.5 wt % | ECZ 20 wt % | Chemical Formula 2A 0.1 wt % |
| Embodiment 2 | PVK 49.4 wt % | PDCST 30 wt % | PCBM 0.5 wt % | ECZ 20 wt % | Chemical Formula 3B 0.1 wt % |
| Embodiment 3 | PVK 49.4 wt % | PDCST 30 wt % | PCBM 0.5 wt % | ECZ 20 wt % | Chemical Formula 3D 0.1 wt % |
| Comparative example | PVK 49.5 wt % | PDCST 30 wt % | PCBM 0.5 wt % | ECZ 20 wt % | — |

Conductivity Characteristics

Figure 3:
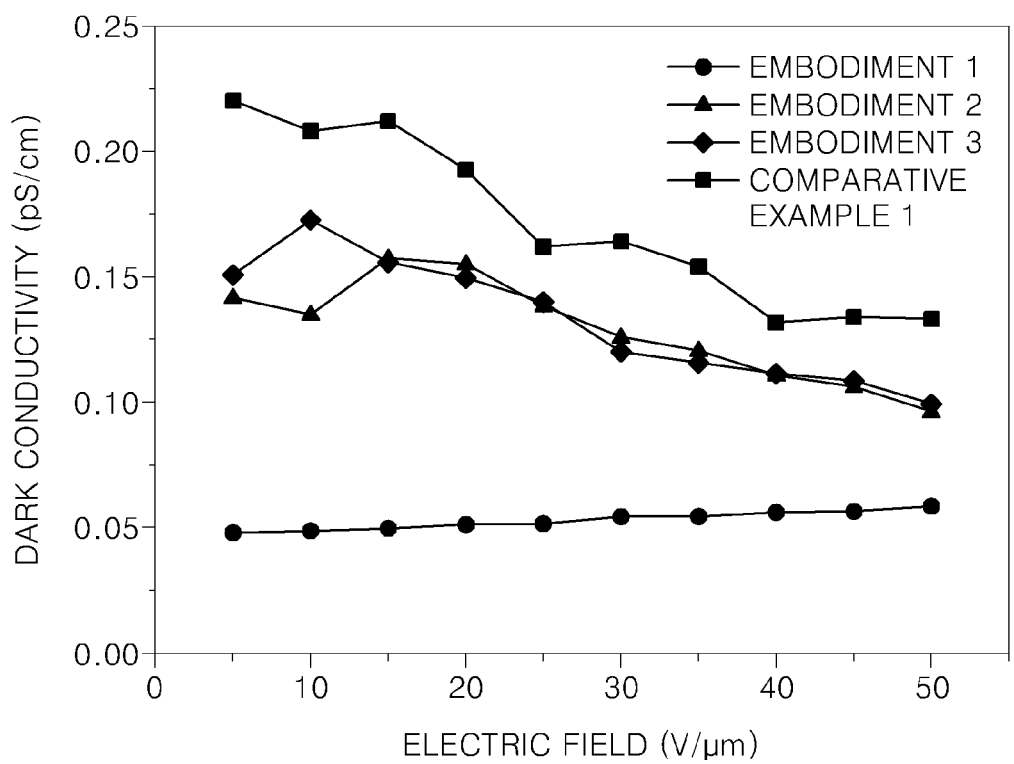

FIG. 3 is a graph of dark conductivity versus electric fields of the photorefractive devices according to Example Embodiment 1-3 and the Comparative Example 1.

The dark conductivity versus the electric field characteristics of FIG. 3 were obtained by measuring electrical conductivity while a voltage is applied to the photorefractive devices under a condition that light is not entering.

Referring to FIG. 3, the photorefractive device of Example Embodiment 1 has the lowest dark conductivity and the dark conductivity of the photorefractive device of Example Embodiment 1-3 have lower dark conductivity than that of the photorefractive device of the Comparative Example 1. This is assuming that the carborane compound effectively traps electrons due to its high electron affinity, and thus, reduces a current. Also, it is assumed that, because the dark conductivity is low, the efficiency of the photorefractive device is increased.

Figure 4:
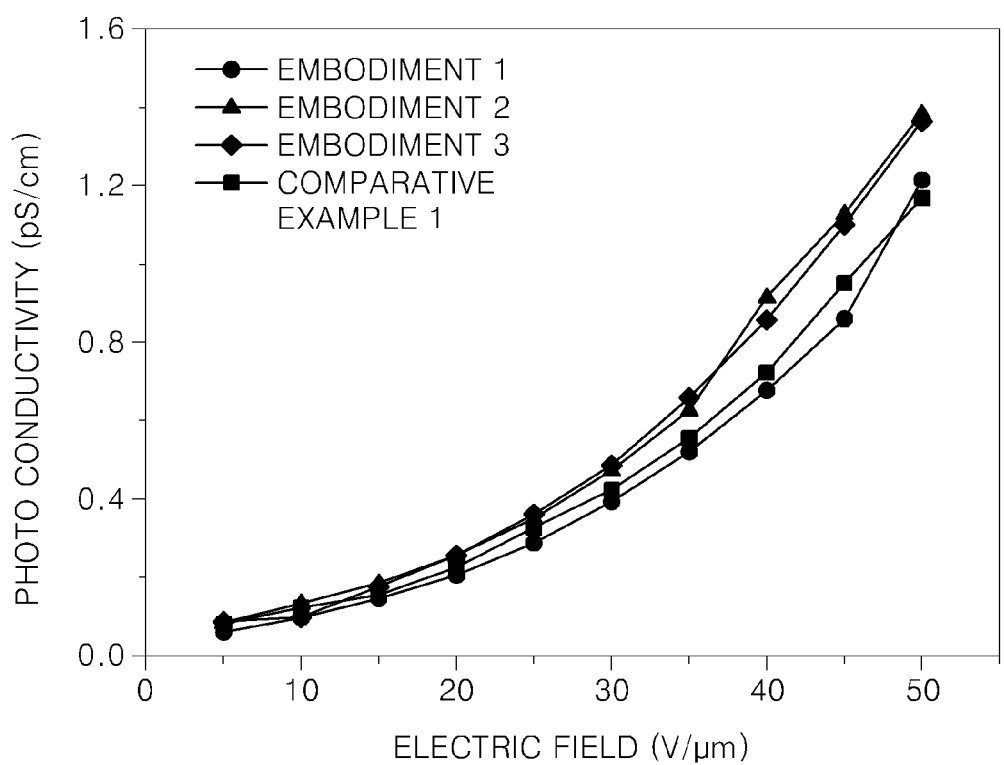

FIG. 4 is a graph of photo conductivity versus electric fields of the photorefractive devices according to Example Embodiments 1-3 and the Comparative Example 1.

The result of the photo conductivity versus electric field characteristics of FIG. 4 was obtained under a condition that a He—Ne laser having a wavelength of 633 nm at 13 mW is irradiated to the photorefractive device.

Referring to FIG. 4, the photo conductivities of the photorefractive devices according to Example Embodiments 2-3 are the highest and those of the photorefractive devices of Example Embodiment 1 and the Comparative Example 1 are nearly similar to each other.

From the above, it can be known that the conductivity characteristics of the photorefractive devices of example embodiments are superior to those of the known photorefractive devices.

The foregoing is illustrative of example embodiments and is not to be construed as limiting thereof. Although a few example embodiments have been described, those skilled in the art will readily appreciate that many modifications are possible in example embodiments without materially departing from the novel teachings. Accordingly, all such modifications are intended to be included within the scope of the disclosure as defined in the claims. Therefore, it is to be understood that the foregoing is illustrative of various example embodiments and is not to be construed as limited to the specific embodiments disclosed, and that modifications to the disclosed embodiments, as well as other embodiments, are intended to be included within the scope of the appended claims.

What is claimed is:

1. A photorefractive composite, comprising:
   at least one carborane compound expressed as the following Chemical Formulae 1A through 1C:

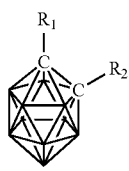

Chemical Formula 1A

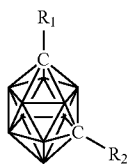

Chemical Formula 1B

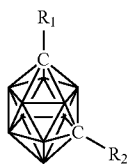

Chemical Formula 1C where, $R_1$ and $R_2$ are, independently from each other, a substituted $C_5$-$C_{60}$ aryl group including at least one carborane group;
a photoconductive polymer; and
a nonlinear optical chromophore,
wherein the photorefractive composite exhibits photoconductivity and optical nonlinearity.

2. The photorefractive composite of claim 1, wherein the at least one carborane compound is at least one compound expressed as the following Chemical Formulae 2N through 2P:

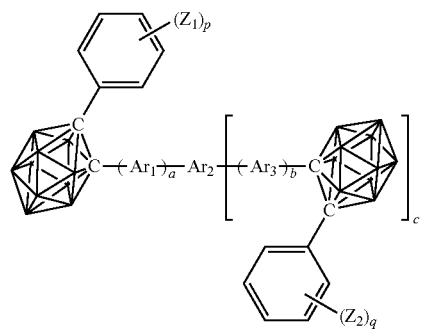

Chemical Formula 2N

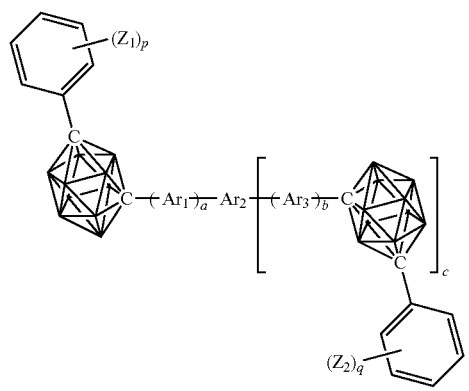

Chemical Formula 2O

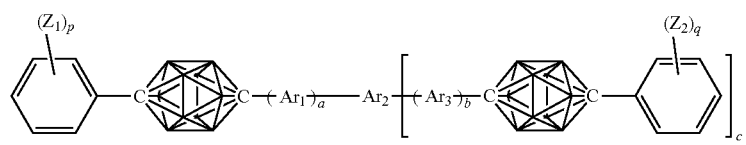

Chemical Formula 2P where, $Z_1$ and $Z_2$ are, independently from each other, one selected from hydrogen atoms, deuterium atoms, halogen atoms, substituted or non-substituted $C_1$-$C_{20}$ alkyl groups, substituted or non-substituted $C_2$-$C_{20}$ alkenyl groups, substituted or non-substituted $C_2$-$C_{20}$ alkynyl groups, substituted or non-substituted $C_1$-$C_{20}$ alkoxy groups, substituted or non-substituted $C_3$-$C_{20}$ cycloalkyl groups, substituted or non-substituted $C_3$-$C_{20}$ cycloalkenyl groups, substituted or non-substituted $C_5$-$C_{20}$ aryl groups, substituted or non-substituted $C_2$-$C_{20}$ heteroaryl groups, substituted or non-substituted $C_5$-$C_{20}$ aryloxy groups, and substituted or non-substituted $C_5$-$C_{20}$ arylthio groups, $Z_1$ and $Z_2$ are the same or different, p and q are integers of 1 through 5, n is an integer of 0 through 10, Ar1, Ar2, and Ar3 are, independently from each other, substituted or non-substituted $C_5$-$C_{20}$ arylene groups, a and b are integers of 0 to 2, and c is an integer of 1 to 5.

3. The photorefractive composite of claim 2, the carborane compound is at least one compound expressed as the following Chemical Formulae 3A through 3D:

Chemical Formula 3A

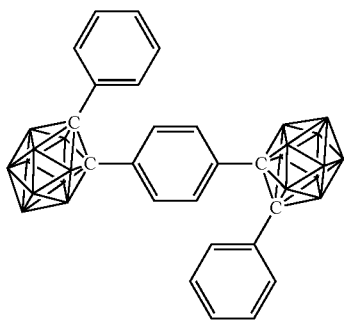

Chemical Formula 3B

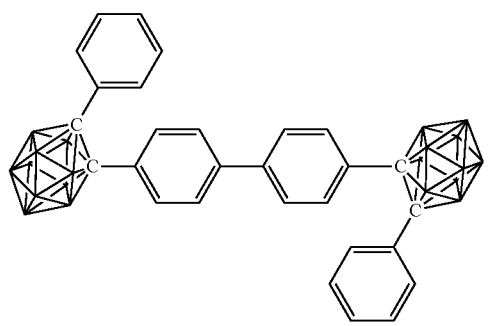

Chemical Formula 3C

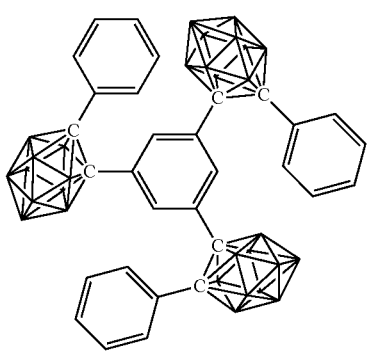

Chemical Formula 3D

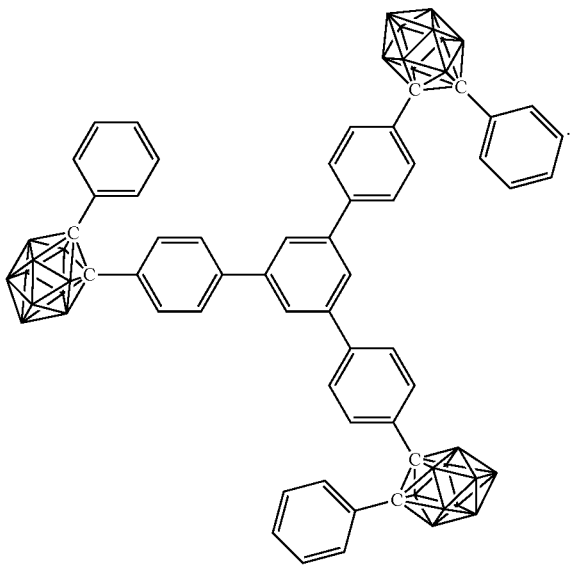

4. The photorefractive composite of claim 1, wherein the at least one carborane compound is present in the photorefractive composite in an amount of about 0.1 parts to about 5 parts by weight with respect to 100 parts by weight of the photorefractive composite.

5. The photorefractive composite of claim 1,
wherein the photoconductive polymer is one selected from the group consisting of polyvinylcarbazole (PVK), polysiloxane carbazole, polyparaphenylenevinylene, polyaniline, polypyrrole, polyacetylene, polythiophene, polyalkylthiophene, poly(alkylthiophene), carbazole-substituted polysiloxane (PSX-Cz), poly(p-phenylene terephthalate) carbazole (PPT-CZ), polyacrylate triphenylamine (TATPD), derivatives thereof, and a mixture of these materials.

6. The photorefractive composite of claim 1,
wherein the photoconductive polymer is present in the photorefractive composite in an amount of about 30 parts to about 60 parts by weight with respect to 100 parts by weight of the photorefractive composite.

7. The photorefractive composite of claim 1,
wherein the nonlinear optical chromophore is one selected from the group consisting of 4-piperidinobenzylidene malononitrile (PDCST), 2,5-dimethyl-4-(p-nitrophenylazo)anisole (DMNPAA), 2,N,N-dihexyl-amino-7-dicyanomethylidenyl-3,4,5,6,10-pentahydronaphthalene (DHADC-MPN), 4-di(2-methoxyethyl)aminobenzylidene malononitrile (AODCST), amino-thienyl-dioxocyano-pyridine (ATOP), fluorinated cyano-tolane chromophore (FTCN), diethylamino-nitrostyrene (DEANST), and a mixture of these materials.

8. The photorefractive composite of claim 1,
wherein the nonlinear optical chromophore is present in the photorefractive composite in an amount of about 20 parts to about 50 parts by weight with respect to 100 parts by weight of the photorefractive composite.

9. The photorefractive composite of claim 1, further comprising:
a photosensitizer.

10. The photorefractive composite of claim 9, wherein the photosensitizer is one selected from the group consisting of $C_{60}$ fullerene, phenyl-$C_{61}$-butyric acid methyl ester (PCBM), 2,4,7-trinitrofluorenone (TNF), 2,4,7-trinitro9-fluorenylidene-malononitrile (TNFDM), and a mixture of these materials.

11. The photorefractive composite of claim 9, wherein the photosensitizer is present in the photorefractive composite in an amount of about 0.1 parts to 3 about parts by weight with respect to 100 parts by weight of the photorefractive composite.

12. The photorefractive composite of claim 9, wherein the photosensitizer is excitable by a light source having a wavelength in a range of about 380 nm to about 740 nm.

13. The photorefractive composite of claim 1, further comprising:
a plasticizer.

14. The photorefractive composite of claim 13, wherein the plasticizer is one selected from the group consisting of ethylcarbazole (ECZ), dimethyl phthalate (DMP), diethyl phthalate (DEP), diisobutyl phthalate (DIBP), dibutyl phthalate (DBP), diheptylphtalate (DHP), di-2-ethylhexyl phthalate (DOP), dioctyl phthalate (DIOP), di-n-octyl phthalate (DnOP), dinonyl phthalate (DNP), diisodecyl phthalate (DIDP), ditridecyl phthalate (DTDP), dicyclohexyl phthalate (DCHP), benzyl butyl phthalate (BBP), butyl lauryl phthalate (BLP), dioctyl adipate (DOA), diisodecyl adipate (DIDA), dioctyl azelate (DOZ), dibutyl sebacate (DBS), dioctyl sebacate (DOS), dioctyl terephthalate (DOTP), diethylene glycol dibenzoate (DEDB), butyl oleate (BO), tricresyl phosphate (TCP), trioctyl phosphate (TOP), triphenyl phosphate (TPP), trichloroethyl phosphate (TCEP), and a mixture of these materials.

15. The photorefractive composite of claim 13, wherein the plasticizer is present in the photorefractive composite in an amount of about 1 part to 20 parts by weight with respect to 100 parts by weight of the photorefractive composite.

16. The photorefractive composite of claim 1,
wherein an electric conductivity of the photoconductive polymer increases when the photoconductive polymer absorbs electromagnetic radiation.

17. The photorefractive composite of claim 1, wherein,
a light absorption region of the at least one carborane compound is in a visible light region, and
the photorefractive composite excludes an additional photosensitizer.

18. A spatial light modulator (SLM), comprising:
a first electrode;
a second electrode corresponding to the first electrode;
a photorefractive layer between the first and second electrodes, wherein the photorefractive layer includes at least one carborane compound expressed as the following Chemical Formulae 1A through 1C:

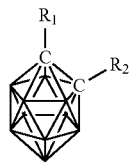

Chemical Formula 1A

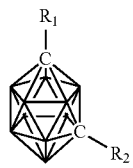

Chemical Formula 1B

Chemical Formula 1C where, $R_1$ and $R_2$ are, independently from each other, a substituted $C_5C_{60}$ aryl group including at least one carborane group;
a photoconductive polymer; and
a nonlinear optical chromophore,
wherein the photorefractive layer exhibits photoconductivity and optical nonlinearity.

19. The SLM of claim 18, wherein the at least one carborane compound is at least one compound expressed as the following Chemical Formulae 2N through 2P:

Chemical Formula 2N

Chemical Formula 2O

Chemical Formula 2P

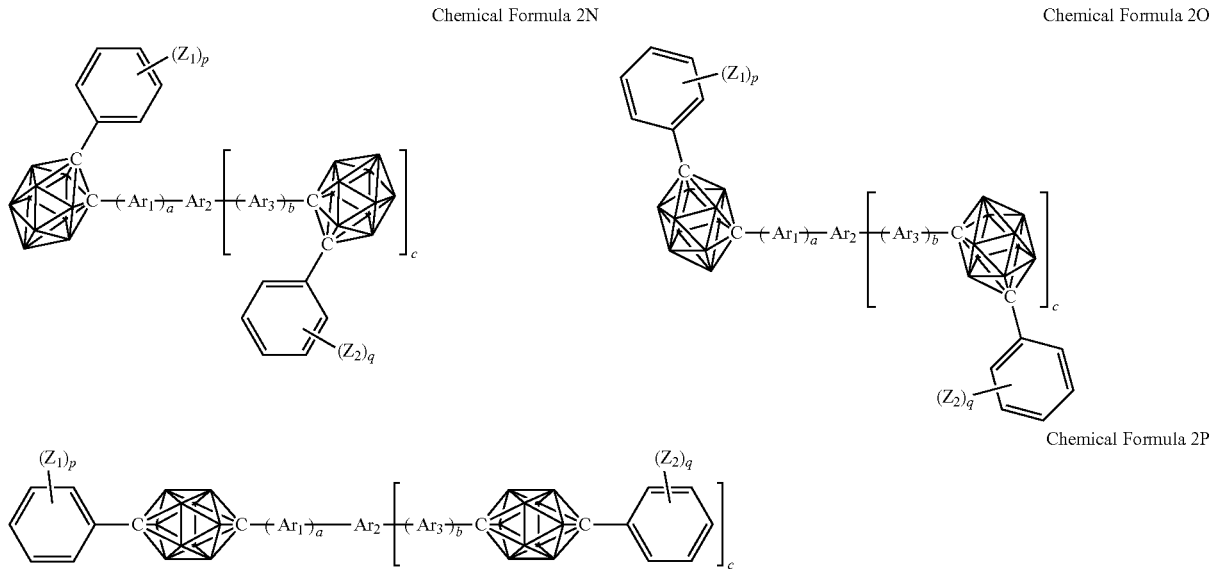

where, $Z_1$ and $Z_2$ are, independently from each other, one selected from hydrogen atoms, deuterium atoms, halogen atoms, substituted or non-substituted $C_1$-$C_{20}$ alkyl groups, substituted or non-substituted $C_2$-$C_{20}$ alkenyl groups, substituted or non-substituted $C_2$-$C_{20}$ alkynyl groups, substituted or non-substituted $C_1$-$C_{20}$ alkoxy groups, substituted or non-substituted $C_3$-$C_{20}$ cycloalkyl groups, substituted or non-substituted $C_3$-$C_{20}$ cycloalkenyl groups, substituted or non-substituted $C_5$-$C_{20}$ aryl groups, substituted or non-substituted $C_2$-$C_{20}$ heteroaryl groups, substituted or non-substituted $C_5$-$C_{20}$ aryloxy groups, and substituted or non-substituted $C_5$-$C_{20}$ arlythio groups, $Z_1$ and $Z_2$ are the same or different, p and q are integers of 1 through 5, n is an integer of 0 through 10, Ar1, Ar2, and Ar3 are, independently from each other, substituted or non-substituted $C_5$-$C_{20}$ arylene groups, a and b are integers of 0 to 2, and c is an integer of 1 to 5.

20. The SLM of claim 18,
wherein the photoconductive polymer is one selected from the group consisting of polyvinylcarbazole (PVK), polysiloxane carbazole, polyparaphenylenevinylene, polyaniline, polypyrrole, polyacetylene, polythiophene, polyalkylthiophene, poly(alkylthiophene), carbazole-substituted polysiloxane (PSX-Cz), poly(p-phenylene terephthalate) carbazole (PPT-CZ), polyacrylate triphenylamine (TATPD), derivatives thereof, and a mixture of these materials.

21. The SLM of claim 18, further comprising:
wherein the nonlinear optical chromophore is one selected from the group consisting of 4-piperidinobenzylidene malononitrile (PDCST), 2,5-dimethyl-4-(p-nitrophenylazo)anisole (DMNPAA), 2,N,N-dihexyl-amino-7-dicyanomethylidenyl-3,4,5,6,10-pentahydronaphthalene (DHADC-MPN), 4-di(2-methoxyethyl)aminobenzylidene malononitrile (AODCST), amino-thienyl-dioxocyano-pyridine (ATOP), fluorinated cyano-tolane chromophore (FTCN), and diethylamino-nitrostyrene (DEANST), and a mixture of these materials.

22. The SLM of claim 18, further comprising:
a photosensitizer.

23. The SLM of claim 22, wherein the photosensitizer is excitable by a light source having a wavelength in a range of about 380 nm to about 740 nm.

24. The SLM of claim 22, wherein the photosensitizer is one selected from the group consisting of $C_{60}$ fullerene, phenyl-$C_{61}$-butyric acid methyl ester (PCBM), 2,4,7-trinitrofluorenone (TNF), and 2,4,7-trinitro-9-fluorenylidene-malononitrile (TNFDM), and a mixture of these materials.

25. The SLM of claim 18, further comprising:
a plasticizer.

26. The SLM of claim 25, wherein the plasticizer is one selected from the group consisting of ethylcarbazole (ECZ), dimethyl phthalate (DMP), diethyl phthalate (DEP), diisobutyl phthalate (DIBP), dibutyl phthalate (DBP), diheptylphthalate (DHP), di-2-ethylhexyl phthalate (DOP), dioctyl phthalate (DIOP), di-n-octyl phthalate (DnOP), dinonyl phthalate (DNP), diisodecyl phthalate (DIDP), ditridecyl phthalate (DTDP), dicyclohexyl phthalate (DCHP), benzyl butyl phthalate (BBP), butyl lauryl phthalate (BLP), dioctyl adipate (DOA), diisodecyl adipate (DIDA), dioctyl azelate (DOZ), dibutyl sebacate (DBS), dioctyl sebacate (DOS), dioctyl terephthalate (DOTP), diethylene glycol dibenzoate (DEDB), butyl oleate (BO), tricresyl phosphate (TCP), trioctyl phosphate (TOP), triphenyl phosphate (TPP), trichloroethyl phosphate (TCEP) and a mixture of these materials.

27. The SLM of claim 18,
wherein an electric conductivity of the photoconductive polymer increases when the photoconductive polymer absorbs electromagnetic radiation.

28. The SLM of claim 18, wherein,
a light absorption region of the at least one carborane compound is in a visible light region, and
the photorefractive composite excludes an additional photosensitizer.

29. A hologram display device, comprising:
a light source unit configured to irradiate light for recording and reproducing a three-dimensional image of an object;
an input unit configured to input three-dimensional image information of the object;

a display unit including the spatial light modulator (SLM) according to 21, wherein the display unit is configured to record the three-dimensional image information of the object input by the input unit and configured to reproduce the three-dimensional image of the object by using the light irradiated from the light source unit; and
an optical system configured to transmit the light irradiated from the light source unit to the input unit and the display unit.

\* \* \* \* \*